(12) United States Patent
Spain, III

(10) Patent No.: US 7,410,155 B2
(45) Date of Patent: Aug. 12, 2008

(54) CLAMP AND SEALER FOR USE ON FLEXIBLE CONDUITS IN BIOPHARMACEUTICAL APPLICATIONS

(76) Inventor: Charles J. Spain, III, 586 Northwoods Country Rd., Tarboro, NC (US) 27886

( * ) Notice: Subject to any disclaimer, the term of this patent is extended or adjusted under 35 U.S.C. 154(b) by 172 days.

(21) Appl. No.: 11/190,569

(22) Filed: Jul. 27, 2005

(65) Prior Publication Data

US 2006/0236829 A1   Oct. 26, 2006

Related U.S. Application Data

(60) Provisional application No. 60/591,655, filed on Jul. 28, 2004.

(51) Int. Cl.
*B23Q 1/25* (2006.01)
(52) U.S. Cl. .............................. 269/71; 29/281.1; 29/559
(58) Field of Classification Search .................. 269/71, 269/73, 900, 901; 29/559, 281.1
See application file for complete search history.

(56) References Cited

U.S. PATENT DOCUMENTS

| | | | |
|---|---|---|---|
| 5,203,548 A * | 4/1993 | Sanders | 269/302.1 |
| 5,238,307 A | 8/1993 | Mooney et al. | |
| 5,350,080 A | 9/1994 | Brown et al. | |
| 5,362,642 A | 11/1994 | Kern | |
| 5,687,993 A | 11/1997 | Brim | |
| 5,853,247 A | 12/1998 | Shroyer | |
| 5,941,635 A | 8/1999 | Stewart | |
| 5,971,379 A * | 10/1999 | Leon, Jr. | 269/8 |
| 5,988,422 A | 11/1999 | Vallot | |
| 5,992,836 A * | 11/1999 | Howe | 269/41 |
| 6,076,457 A | 6/2000 | Vallot | |
| 6,086,574 A | 7/2000 | Carroll et al. | |
| 6,186,932 B1 | 2/2001 | Vallot | |
| 6,279,408 B1 | 8/2001 | Lewis | |
| 6,418,801 B1 | 7/2002 | Lewis | |
| 6,427,993 B1 * | 8/2002 | Prochac | 269/37 |
| 6,543,495 B2 | 4/2003 | Hougland | |
| 6,578,440 B2 | 6/2003 | Lewis | |
| 6,582,653 B1 | 6/2003 | Warburton-Pitt | |
| 6,712,963 B2 | 3/2004 | Schick | |
| 6,994,335 B2 * | 2/2006 | Porchia et al. | 269/302.1 |
| 2002/0065505 A1 | 5/2002 | Willemstyn | |
| 2003/0006610 A1 | 1/2003 | Werth | |
| 2003/0193190 A1 | 10/2003 | Werth | |
| 2004/0028555 A1 | 2/2004 | Warburton-Pitt | |
| 2004/0089828 A1 | 5/2004 | Werth | |

* cited by examiner

*Primary Examiner*—Lee D Wilson
(74) *Attorney, Agent, or Firm*—Coats & Bennett, P.L.L.C.

(57) ABSTRACT

A clamp for clamping and sealing a flexible or deformable conduit extending between a supply and a receiving or holding container. The clamp includes upper and lower sections that can be moved from an open to a closed position. In a closed position the clamp engages the flexible tube or conduit and seals the same, thereby preventing fluid from passing past the seal. The clamp includes two half sections, and can be cut and separated such that each half section clamps and seals a portion of the flexible or deformable conduit or tube. In use, the clamp is typically used to clamp and seal a flexible tube, such as a silicon tube extending between a supply and a receiving container of the type employed in handling biopharmaceutical fluids.

21 Claims, 7 Drawing Sheets

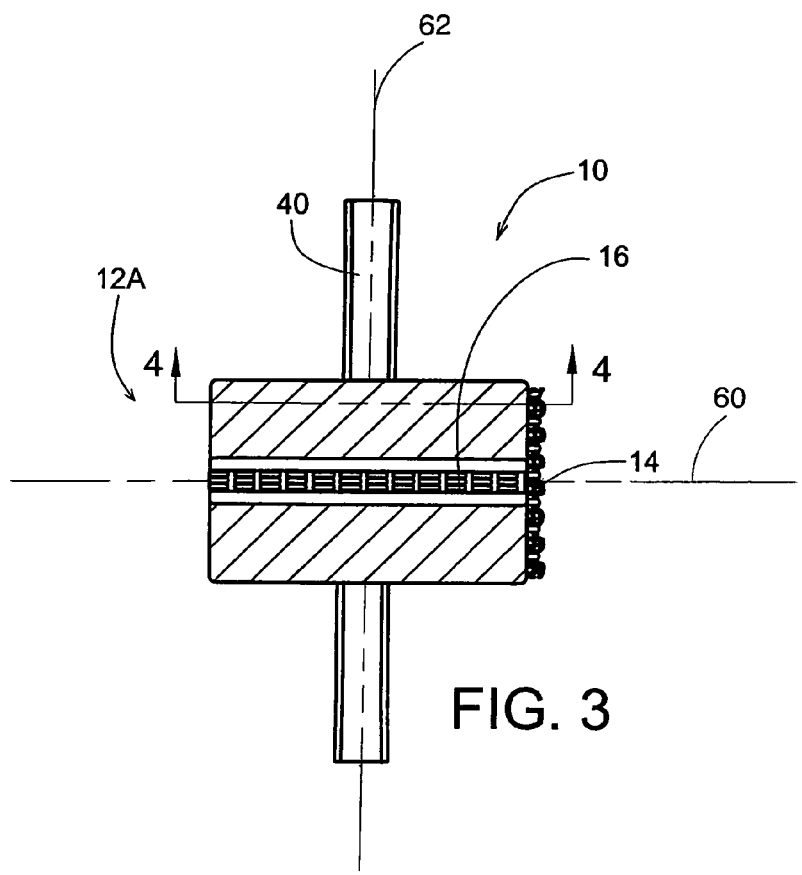
FIG. 3
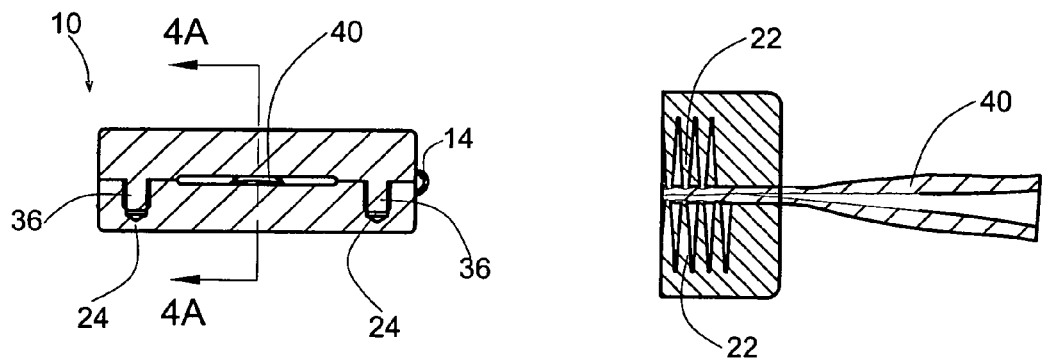
FIG. 4
FIG. 4A

CLAMP AND SEALER FOR USE ON FLEXIBLE CONDUITS IN BIOPHARMACEUTICAL APPLICATIONS

CROSS REFERENCE TO RELATED PROVISIONAL APPLICATION

This application claims priority under 35 U.S.C. § 119(e) from the following U.S. provisional application: application Ser. No. 60/591,655 filed on Jul. 28, 2004. That application is incorporated in its entirety by reference herein.

FIELD OF INVENTION

The present invention relates to a clamp and sealer for engaging a flexible tube that is utilized to convey biotechnology or pharmaceutical fluids.

BACKGROUND OF THE INVENTION

The handling and transfer of biotechnology and pharmaceutical compositions requires that great care be exercised to maintain these compositions free from contamination. For example, it is common to transfer these fluids or compositions from a supply tank to a sample bag. Often a silicon tube is utilized between the supply tank and the sample bag. Typically the biotechnology or pharmaceutical fluid is manufactured or stored in the supply tank. From the supply tank, the fluid or composition is pumped or directed through the silicon tube to a receiving receptacle such as a sample bag. Once the receiving receptacle or sample bag is filled, it follows that the sample bag has to be detached or decoupled from the supply. This, of course, means that the sample bag has to be decoupled or separated from the supply, or the silicon tube leading from the supply, in such a way that the contents within the sample bag is not contaminated.

SUMMARY OF THE INVENTION

The present invention entails a clamp for clamping and sealing a conduit or tube where the clamp includes two sections and wherein each of the sections include separable first and second portions.

The present invention further entails a clamp for clamping and sealing a conduit, such as a silicon tube. The clamping device includes an upper section and a lower section with the upper and lower sections being hinged together. The conduit to be sealed is extended between the upper and lower sections and the sections are brought together and effectively clamp the conduit or tube therebetween. The clamp includes a series of locking studs that are formed on one section of the clamp and which are adapted to project into locking apertures formed in the other section of the clamp. Once the two sections are secured together, the tube or conduit extending therebetween is securely clamped and a fluid seal is effectively formed across the conduit or tube.

In one particular embodiment, the clamp includes two half sections secured together by a structure that permits the half sections to be easily separated. In particular, in the case of one embodiment, the clamp is provided with a flexible material interconnecting the two half sections of the clamp. Once the clamp is locked and secured about the tube or the conduit, this flexible material can be cut with a pair of scissors or shear, thereby separating the two half sections.

The present invention further entails a method of clamping and cutting a deformable conduit or tube. This method includes extending the tube between first and second sections of a clamp and clamping the tube by closing the first and second sections on the tube. Each section includes at least two portions that are separable. The method entails separating each section into first and second portions so as to divide the clamp and the first and second sections into two parts with each part including a portion of the first and second sections. The method includes cutting the tube between the two parts so as to leave at least one portion of the tube clamped with at least one part of the first and second sections.

Other objects and advantages of the present invention will become apparent and obvious from a study of the following description and the accompanying drawings which are merely illustrative of such invention.

BRIEF DESCRIPTION OF THE DRAWINGS

FIG. 3 is a top plan view of the clamp of the present invention shown in a closed position and clamping a conduit.

FIG. 4 is a cross sectional view taken through the line 4-4 of FIG. 3.

FIG. 4A is a cross sectional view taken through the line 4A-4A of FIG. 4.

DESCRIPTION OF THE INVENTION

Figure 1:
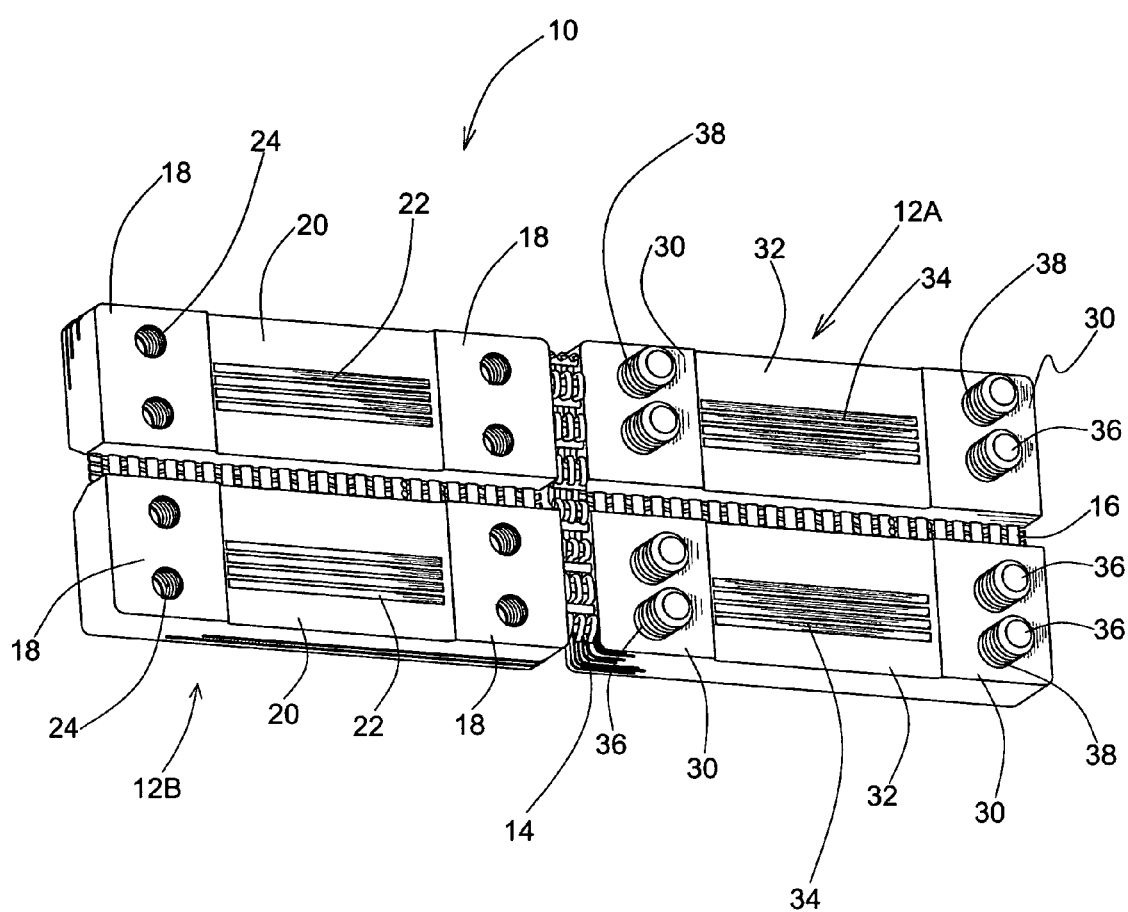
FIG. 1 is a perspective view of the clamp of the present invention shown in an open position.

With reference to the drawings, the clamp of the present invention is shown therein and indicated generally by the numeral 10. Clamp 10 is sometimes referred to as a conduit sealer because it is designed to clamp and seal a deformable tube or conduit such as a silicon tube. As will be appreciated from subsequent portions of this disclosure, the clamp 10 can be inserted around a deformable conduit and clamped there against and in the process the clamp will effectively seal the conduit such that fluid cannot pass through the tube in the area where the tube is clamped.

Viewing clamp 10 in more detail, it is seen that the same includes a housing. The housing for clamp 10 can be constructed of various materials such as plastic, metal, wood, etc. As illustrated in the drawings the housing includes two sections, an upper section indicated generally by 12A and a lower section indicated generally by 12B. Interconnecting the upper and lower sections 12A and 12B is a hinge or connector 14. Hinge 14 can be referred to as a living hinge in that it is of a relatively simple construction. In the case of this embodiment, hinge 14 is constructed of a flexible fabric material that provides substantial strength to hold the upper and lower sections 12A and 12B together and which permits the upper and lower sections 12A and 12B to be moved between an open position shown in FIG. 1 and a closed position shown in FIG. 2. While hinge 14 has sufficient strength to connect the upper and lower sections 12A and 12B together, the hinge structure itself is of a design that permits the same to be cut. As will be appreciated subsequently herein, the clamp 10 is said to include two half sections that can be separated from each other. In separating the half sections, it will be necessary to cut through or break the hinge 14.

Each of the sections 12A and 12B are separable into two parts, sometimes referred to as first and second parts. Note in FIG. 1 where section 12A includes two half sections that are spaced apart. These two half sections are sometimes referred to as first and second parts. Note also that section 12B includes a like structure, that is two half sections that are spaced apart.

The first and second parts of each section 12A or 12B are generally held together by a connector 16. In FIG. 1 the connector 16 is shown extending across both sections 12A and 12B. It is understood that the connector 16 could be continuous or broken into two parts where one part of the connector 16 would connect the two parts or half sections of 12A and another connector would connect the half sections or the two parts of section 12B.

Functionally, connector 16 serves to hold the two halves together. However, once the clamp 10 is secured around a hose or conduit, connector 16 will be cut thereby separating the two half sections of the clamp and in the process, cutting the conduit or tube held by the clamp 10. Connector 10 can be constructed of various materials. In the embodiment illustrated herein, it is contemplated that the connector 16 would be made of a flexible material such as a fabric construction that would permit the connector 16 to be easily cut by scissors or a shear.

Turning now to a discussion of the lower section 12B, and with particular reference to FIG. 1, it is seen that the lower section includes a series of pads 18. Extending between the pads 18 is an indented center surface 20. Extending transversely across the center surface 20 is a series of spaced apart ribs or ridges 22. Note that the ribs 22 extend generally transversely between opposing pads 18 for each of the half sections that make up the lower section 12B. Formed in each pad 18 is a pair of apertures or bores 24. These apertures or bores 24 extend a selected depth into the pads. Formed around the surface of the apertures or bores is a series of circumferential ribs. These apertures or bores 24 are sometimes referred to as stud receptors.

Turning to the upper section 12A, the upper section includes a series of pads 30. Note that the pads 30 are generally of the same size as the pads 18 formed on the lower section 12B. Thus, when the two sections, 12A and 12B are closed, the pads 30 of the upper section 12A will align with and overlay the pads 18 of the lower section 12B. Further, there is provided an indented center section 32 that extends between opposing pads 30. Like the lower section 12B, the upper section 12A includes a series of spaced apart transversely extending ribs or ridges 34. These ribs 34 extend transversely between opposed pads 30 and align with the ribs 22 of the lower section where the clamp 10 is closed.

Further upper section 12A includes a series of locking studs 36. In the case of this embodiment, the upper section 12A includes four pads 30. Each pad includes a pair of locking studs 36 extending therefrom. Formed around the circumference of each locking stud 36 is a series of ribs 38.

Locking studs 36 are spaced so as to align and mate with the stud receptors 24 formed in the pads 18 of the lower section 12B. That is, when the clamp 10 is closed, the respective locking studs 36 align with and are inserted downwardly into the locking stud receptors 24. The ribs 38 on the locking studs 36 are designed such that the locking studs 36 can be inserted downwardly into the apertures or bores 24, but once inserted therein cannot be retracted. That is, the ribs 38 formed around the locking studs 36 are particularly angled such that they can be extended downwardly past the ribs that are formed about the apertures or bores 24. Once the ribs 38 of the locking studs 36 have been pushed downwardly past the ribs formed about the apertures or bores 24, the angular orientation of the ribs 38 with respect to the ribs formed about the apertures or bores 24 is such that the locking stud cannot easily be withdrawn from the apertures or bores 24.

The areas of the upper and lower sections 12A and 12B that extend between the pads 18 and 30, are designed to receive a tube or conduit 40 to be clamped and sealed. The ridges or ribs 22 and 34 project slightly away from the center surfaces 20 and 32 of the two sections 12A and 12B. Thus the upper edges of the ribs 22 and 34 are elevated above the adjacent surfaces 20 and 32 respectively. Further, the individual upper edges of the ribs 22 and 34 are slightly spaced apart. Thus, when a deformable or flexible conduit or tube 40 is placed therebetween and the clamp 10 is closed, it is appreciated that the tube or conduit will be engaged at two axially spaced locations. Each location engaged will be surrounded by the set of ribs 22 from the lower section 12B and the set of ribs 34 from the upper section 12A.

Figure 2:
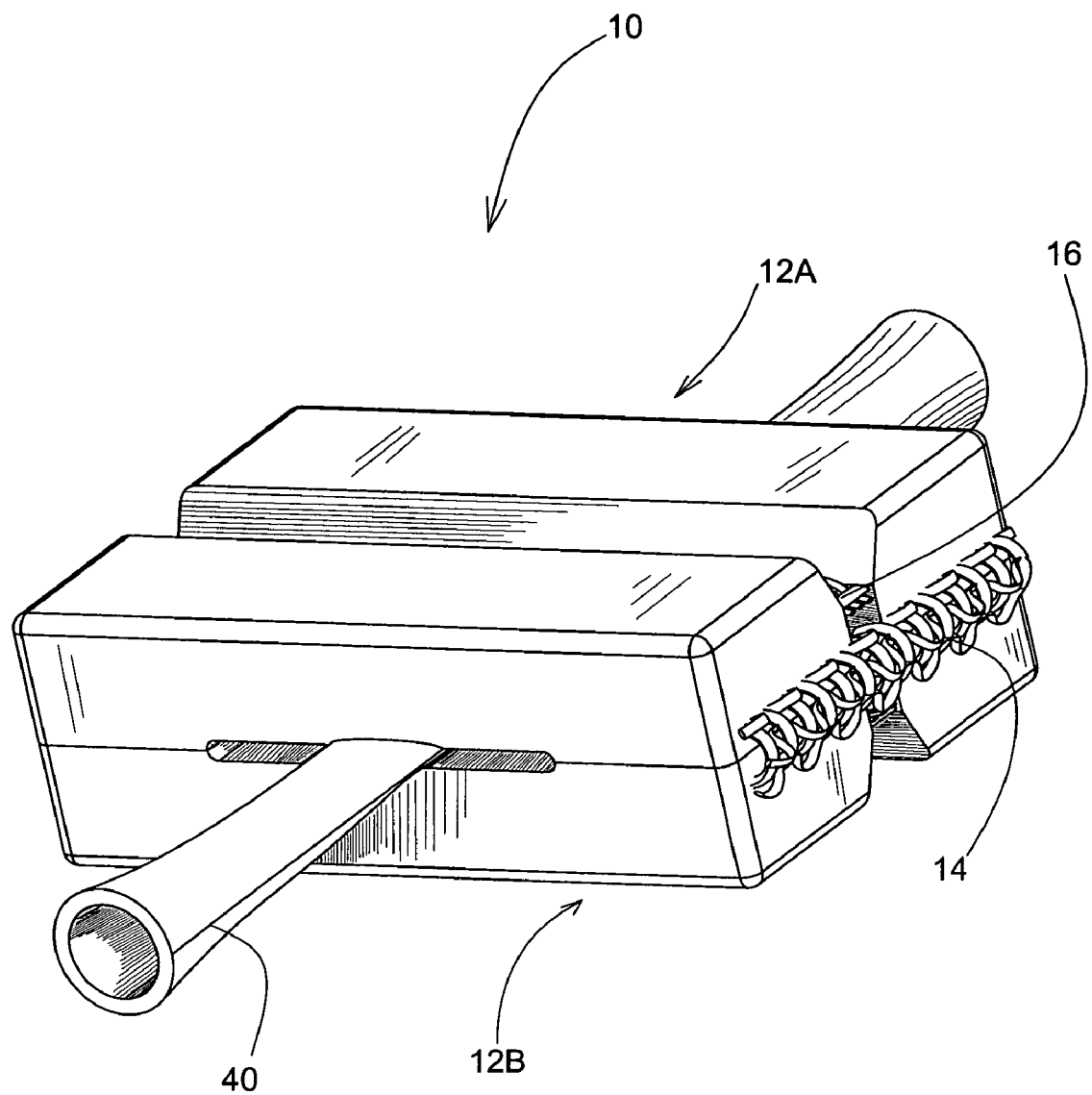
FIG. 2 is a perspective view of the clamp of the present invention shown in a closed position, clamping a deformable conduit.

With particular reference to FIG. 2, a silicon tube 40 is shown secured within the clamp 10. Note that the clamp 10 is disposed in a closed (clamped) position and that the portions of the silicon tube 40 held within the clamp assumes almost a flat horizontal shape. See FIG. 4 for example.

Once the silicon tube 40 is secured within the clamp 10, it follows that the silicon tube 40 will be effectively sealed by each half section or port of the clamp 10. That is, silicon tube 40 will be clamped and sealed at two axial locations disposed on either side of the connector 16.

At this point, the clamp 10 can be separated or split into half sections. This is typically performed by a pair of scissors, a shear or another type of cutting device that is used to cut the connector 16 as well as the hinge 14. In particular, as viewed in FIG. 3, a pair of scissors or shear can be utilized to cut the connector 16. In the process it is appreciated that as the connector 16 is cut so will be the silicon tube 40 extending through the clamp 10. Moreover, the hinge 14 will also be cut in the area thereof adjacent the connector 16. This will leave two half sections of the clamp 10 separated. Each half section of the clamp 10 will of course remain clamped and sealed against a terminal end portion of the silicon tube 10. That is, fluid cannot flow through the clamp and seal portion of the tube 40.

Two construction lines are shown in FIG. 3, a transverse construction line 60 and an axis line 62. Transverse line 60 is drawn to illustrate that the upper section 12A shown in FIG. 3 includes two separable parts that are spaced apart and which lie on both sides of the transverse line 60. The term "transverse line" as used herein is simply a term that illustrates or denotes the separable feature of each of the sections 12A and 12B. That is, the transverse line 60 is a reference line and is applicable to both sections 12A and 12B and is used to denote that the respective sections are separable into two parts. Also, the term "transverse" as used herein means that the sections 12A and 12B are separable generally along a line or area that extends transverse to the axis 62 of the tube 40 when the tube is held within the clamp 10.

Figure 5:
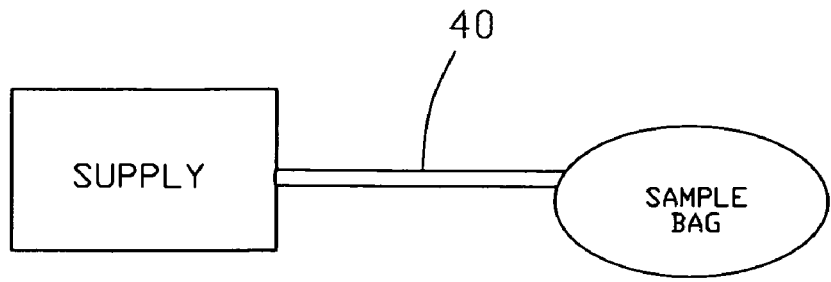
FIG. 5 is a schematic illustration showing a conduit adapted to transmit a biopharmaceutical composition from a supply to a sample bag.
Figure 6:
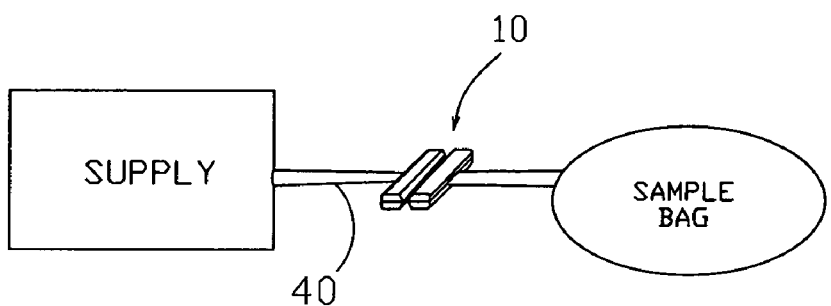
FIG. 6 is a schematic illustration similar to FIG. 5, but with the clamp of the present invention secured to the conduit.
Figure 7:
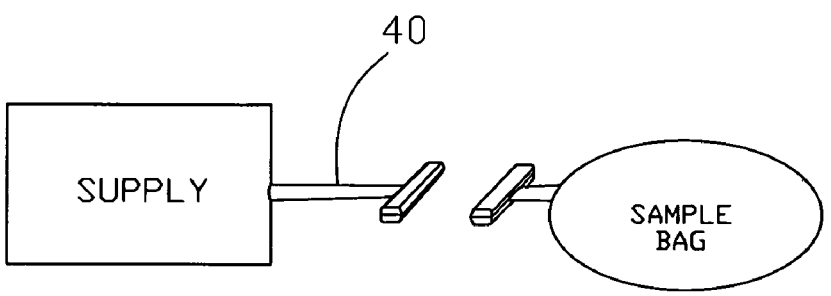
FIG. 7 is a view similar to FIGS. 5 and 6, but illustrating the two half sections of the clamp being cut and separated.

An example of the use of the clamp 10 is illustrated in FIGS. 5-7. In this illustration, there is shown a tube 40, such as a silicon tube, extending from a supply source to a sample bag. For example, the supply source could be biopharmaceutical process equipment or a single-use process bag containing biopharmaceutical compositions. The biopharmaceutical composition is pumped or directed from the machine or supply through the conduit 40 to a receiving container or receptacle such as a small sample bag. In this case the schematic illustrates a sample bag. Once the sample bag is filled it must be disconnected from the supply or manufacturing machine in such a way that its contents are protected against contamination. In order to accomplish that, the clamp 10 of the present invention is inserted and clamped onto the tube extending between the supply and the sample bag. Once both half sections of the clamp 10 are securely clamped and sealed around the tube end, then the connector 16, as discussed above, is cut. Once cut, as shown in FIG. 7, the sample bag along with a portion of the tube or conduit and a half section of the clamp 10 can be moved and transported. As shown in FIG. 7, the sample bag is securely clamped and sealed and the contents therein can be transported to another destination in a sealed and contaminant free environment.

Figure 8:
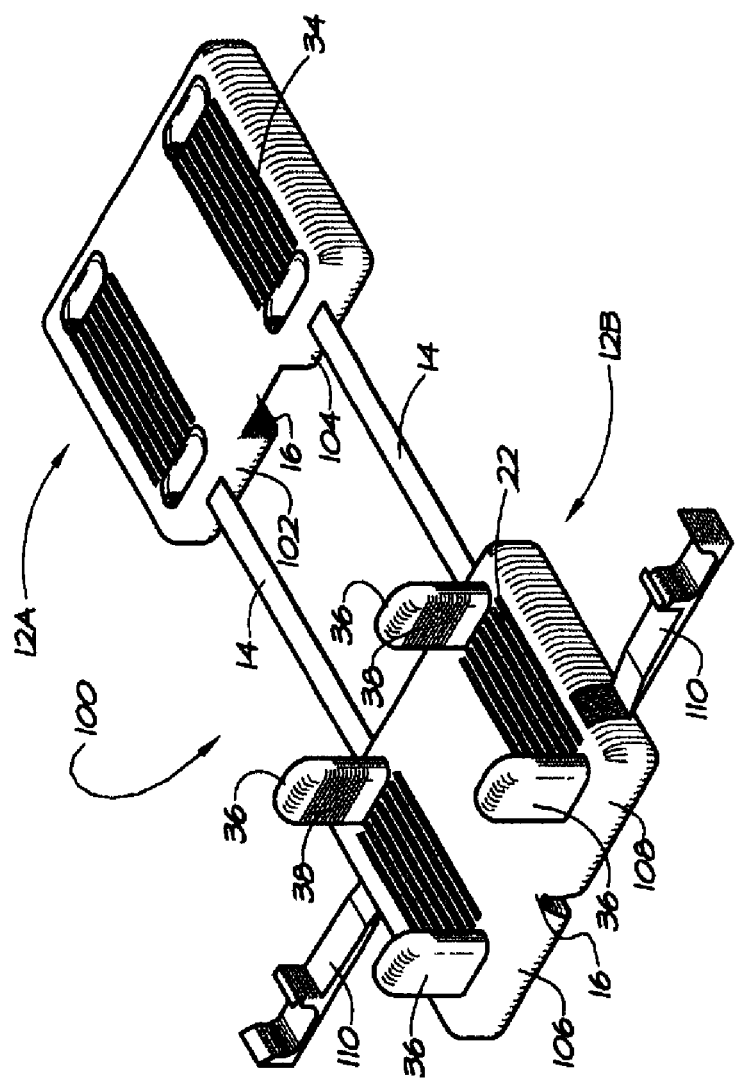
FIG. 8 is a perspective view of an alternate embodiment for the clamp.
Figure 9:
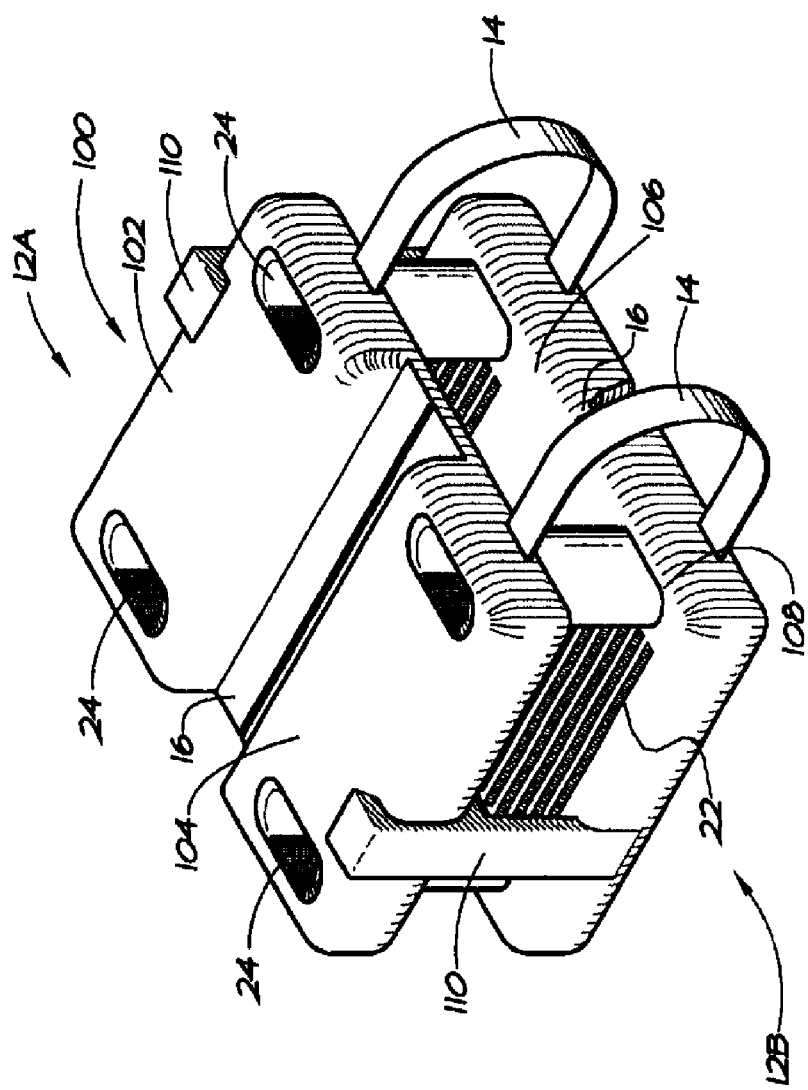
FIG. 9 is a perspective view of the clamp of FIG. 8 shown in a shipping configuration.
Figure 10:
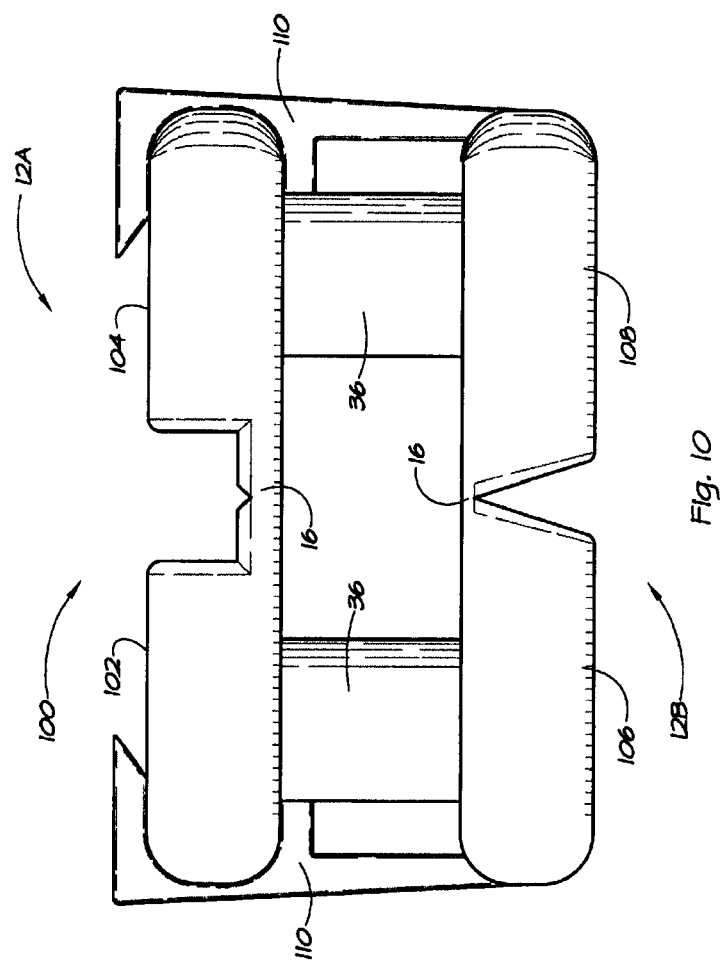
FIG. 10 is a side elevational view of the clamp as shown in FIG. 9.

Turning to FIGS. 8-10, a second embodiment for the clamp is shown therein and indicated generally by the numeral 100. Clamp 100, similar to the clamp discussed herein above, includes two sections indicated generally by the numerals 12A and 12B. Each of the sections 12A and 12B include separable parts or half sections. For example, section 12A includes part or half section 102 and part or half section 104. Likewise, section 12B includes two parts or half sections 106 and 108. As noted above these parts or half sections of each full section is separable. For example, note that section 12A includes a cutout or void that extends transversely across the same. This cutout or void forms a connecting element or connector 16 that effectively couples parts 102 and 104 together. The thin strip of material, which in this case would preferably comprise a molded plastic material, can be cut or severed so as to separate section 12A into individual parts 102 and 104. Likewise, section 12B includes the two separable sections or parts 106 and 108. In this case there is a V-shaped configuration formed generally midway of the section 12B and which extends transversely across. This is particularly illustrated in FIG. 10. In FIG. 10, at the top of the inverted V there is a thin portion of material that effectively holds parts 106 and 108 together. Again, this portion of the section 12B can cut or shear so as to separate section 12B into two parts, 106 and 108.

Clamp 100 shown in FIGS. 8-10 also include a hinge 14 in the form of two straps that connect sections 12A with 12B.

Further, one of the sections is provided with a series of studs or legs 36. Formed in the opposite section is a series of slots or receptors 24 for receiving the studs or legs 36. In the case of this design, the studs or legs 36 would be provided with a series of locking indentions 38. The receptors or slots 24 would be provided with mating locking elements. In this embodiment it is contemplated that the locking studs or legs 36 and the receptors or slots 24 would function similar to conventional tie locks. That is, once the studs or legs 36 are inserted into the receptors 24, the locking elements 38 on the studs 36 in cooperation with the locking elements within the receptors or slots 24 would create an irreversible locking arrangement. That is, the studs or legs 36 could be projected downwardly through the receptors or slots 24, but could not be reversed and removed.

As discussed with the first embodiment, each of the sections 12A and 12B include dual sets of ribs 34. These ribs, when the clamp 100 is closed or locked, engage the deformable tube 40 and compress, close and seal the same.

The clamp 100 is provided with a pair of locking handles 110 that are specifically used when the clamp 100 assumes the transport mode, as shown in FIG. 9. Locking handles 110 can be pivoted from the position shown in FIG. 8 to the position shown in FIG. 9 where the remote ends engage a portion of the opposed section. Effectively, the locking handles 110 prevent the studs or legs 36 from being engaged with the receptors 24. Thus, in transport, the locking handles 110 function to prevent the two sections 12A and 12B from becoming interlocked, and effectively maintain the sections 12A and 12B in spaced apart relationship such that a locking arrangement does not occur.

The present invention has many advantages. One of the principal advantages is that the clamping structure of the present invention is simple, effective and easy to use. In systems and methods involving biological and pharmaceutical composition, the clamp of the present invention can be a cost effective way of preventing sample bags and containers holding such compositions from being contaminated.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

The invention claimed is:

1. A method of clamping and cutting a deformable tube, comprising:
   a. extending the tube between first and second sections of a clamp;
   b. clamping the tube by closing the first and second sections on the tube;
   c. separating each section into first and second portions so as to divide the clamp and the first and second sections into two parts with each part including a portion of the first and second sections;
   d. cutting the tube between the two parts so as to leave at least one portion of the tube clamped with at least one part of the first and second sections;
   e. wherein the clamp includes at least two locking devices with at least one locking device disposed with each part of the clamp such that when the clamp is divided into two parts at least one part of the clamp will remain clamped on the tube.

2. The method of claim 1 wherein cutting the tube includes cutting a connector that connects first and second portions of each section while the tube is clamped by at least one portion of each of the first and second sections.

3. The method of claim 2 wherein the connector is a pliable material.

4. The method of claim 3 wherein the pliable material can be cut by a pair of scissors or a shearing device.

5. The method of claim 1 wherein the tube conveys a pharmaceutical composition from a supply to a sample bag, and wherein after cutting the tube, a portion of the tube extends from the sample bag containing the pharmaceutical composition and is clamped.

6. The method of claim 1 including clamping the tube by projecting at least one locking stud from a first section into a lock and stud receptor formed in the second section.

7. The method of claim 1 wherein in clamping the tube opposed ribs associated with the first and second sections clamp down on the tube.

8. A clamp for clamping a deformable tube comprising:
   a. a first section;
   b. a second section;
   c. the first and second sections being movable with respect to each other between an open position and a clamped position wherein in the open position the tube can be positioned to be clamped by the first and second sections, and in the clamped position the tube lies between the first and second positions;

d. the first section being separable about a transverse line into first and second parts;

e. the second section being separable about a transverse line into first and second parts;

f. at least two locking devices with at least one locking device disposed on each side of the transverse lines such that when the first and second parts of each section are separated, at least one portion of the clamp will remain clamped on the tube.

9. The clamp of claim 8 including a first connector connecting the first and second sections together; a second connector connecting the first and second parts of the first section; and a third connector connecting the first and second parts of the second section.

10. The clamp of claim 9 wherein the second and third connectors are pliable and which may be cut by a pair of scissors or a shearing device.

11. The clamp of claim 9 including at least two locking studs and at least locking stud receptors, and wherein at least one locking stud and at least one locking stud receptor is disposed on each side of the second and third connectors.

12. The clamp of claim 9 wherein the first connector extends generally perpendicular to the second and third connectors.

13. The clamp of claim 8 including one or more locking studs projecting from one of the sections and one or more locking stud receptors formed in the other section such that in a locked position the one or more locking studs project into the one or more locking receptors.

14. The clamp of claim 8 including at least two locking studs and at least two locking stud receptors, wherein at least one locking stud and at least one locking stud receptor is disposed on each side of the transverse lines.

15. The clamp of claim 8 including a hinge connecting the first and second sections together, and wherein the first section is separable into first and second parts about the transverse line that extends generally perpendicular to the length of the hinge; and wherein the second section is separable into first and second parts about the transverse axis that extends generally perpendicular to the length of the hinge.

16. The clamp of claim 8 wherein the tube, when clamped within the clamp, includes a longitudinal axis, and wherein the transverse lines denoting the separable section extend generally normal to the longitudinal axis of the tube.

17. The clamp of claim 9 wherein the second and third connectors are designed to be cut such that the clamp is divided into a first clamping portion and a second clamping portion.

18. A clamp for clamping a deformable tube, comprising:
a. a first section;
b. a second section;
c. a hinge interconnecting the first and second sections together such that the first and second sections can be moved from an open position to a closed position;
d. the first section including two spaced apart and separable portions;
e. a first connector interconnecting the two spaced apart portions of the first section;
f. the second section including spaced apart and separable portions;
g. a second connector interconnecting the two spaced apart portions of the second section;
h. a plurality of locking studs extending from at least two portions of the sections;
i. a plurality of locking stud receptors formed in at least two portions of the sections such that when the sections assume the closed position the locking studs project into and lock within the locking stud receptors; and
j. a series of ribs formed in at least one section for engaging and clamping down on the deformable tube when the sections assume the closed position.

19. The clamp of claim 18 wherein there is provided two sets of opposed ribs, one set of ribs being formed in the first section and another set of ribs formed in the second section.

20. The clamp of claim 18 wherein the first and second connectors are pliable and are adapted to be cut with a pair of scissors or a shearing device.

21. The clamp of claim 18 wherein the hinge is disposed generally perpendicular to the first and second connectors.

* * * * *